United States Patent [19]

Kise et al.

[11] Patent Number: 5,011,831
[45] Date of Patent: Apr. 30, 1991

[54] DERIVATIVES OF QUINOLINECARBOXYLIC ACID

[75] Inventors: Masahiro Kise; Masahiko Kitano, both of Kyoto; Masakuni Ozaki, Joyo; Kenji Kazuno, Rittocho; Masahito Matsuda, Otsu; Ichiro Shirahase, Kyoto; Yoshifumi Tomii, Katano, all of Japan

[73] Assignee: Nippon Shinyaku Co. Ltd., Japan

[21] Appl. No.: 267,938

[22] Filed: Nov. 7, 1988

[30] Foreign Application Priority Data

Nov. 7, 1987 [JP] Japan .................. 62-281551

[51] Int. Cl.$^5$ .................. A61K 31/395; C07D 513/04
[52] U.S. Cl. .................. 514/210; 546/80; 544/60; 544/98; 544/111; 544/238; 544/333; 544/361; 544/405
[58] Field of Search .............. 546/80; 514/210, 228.8, 514/233.2, 228.2, 254, 256; 544/98, 111, 56, 60, 361, 405, 333, 238

[56] References Cited

U.S. PATENT DOCUMENTS 4,659,734  4/1987  Enomoto et al. .................. 546/80

FOREIGN PATENT DOCUMENTS 0058392  8/1982  Japan .................. 546/80

*Primary Examiner*—Frederick E. Waddell
*Assistant Examiner*—Catherine Scalzo
*Attorney, Agent, or Firm*—Jacobs & Jacobs

[57] ABSTRACT

Quinolinecarboxylic acid derivatives of the formula (I)

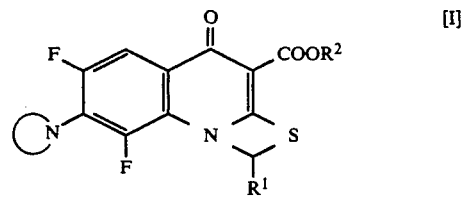

and pharmaceutically acceptable salts thereof wherein $R^1$ is hydrogen, straight or branch chain lower alkyl or phenyl unsubstituted or substituted by one or more halo moieties; $R^2$ is hydrogen or straight or branch chain lower alkyl; and

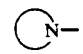

is a 5- or 6-membered ring wherein the nitrogen atom is the only heteroatom or where there is a second heteroatom selected from the group consisting of nitrogen, oxygen and sulfur, said 5- or 6-membered ring being unsubstituted or substituted by lower alkyl, amino or mono- or di-lower alkyl amino are useful for treating bacterial infections in humans and animals.

21 Claims, No Drawings

DERIVATIVES OF QUINOLINECARBOXYLIC ACID

The present invention is concerned with quinolinecarboxylic acid derivatives and pharmaceutically acceptable salts thereof which are useful for treating bacterial infections in humans and animals.

Nalidixic acid, piromidic acid, pipemidic acid, enoxacin (AT-2266), ofloxacin (DL-8280), and the like are known in the art and have been widely used as synthetic antibacterial agents for the treatment of gram-negative bacteria infections. However, these substances are not satisfactory for the treatment of gram-positive bacterial infections nor are they satisfactory for the treatment of chronic infectious diseases caused by *Pseudomonas aeruginosa*.

The present inventors have found quinolinecarboxylic acids to have antibacterial activity and have filed a Japanese Patent Application No. 79993/1987 directed thereto. In that application, there is a disclosure that thiazetoquinolinecarboxylic acids in which there is a chlorine or bromine atom at the 8-position but there is no disclosure of thiazetoquinolinecarboxylic acids having a fluorine atom at the 8-position according to the instant invention. Although the 8-chloro and 8-bromo compounds exhibit good antibacterial activity, they have not proven to be fully satisfactory on administration to humans and animals.

One of the objects of the present invention was to develop antibacterial agents having better antibacterial activity and lower toxicity than previously known antibacterial agents.

More particularly, the present invention is concerned with quinolinecarboxylic acid derivatives of the formula (I)

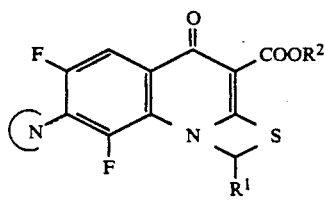

and pharmaceutically acceptable salts thereof wherein $R^1$ is hydrogen, straight or branch chain lower alkyl or phenyl unsubstituted or substituted by one or more halo moieties; $R^2$ is hydrogen or straight or branch chain lower alkyl; and

is a 5- or 6- membered ring wherein the nitrogen atom is the only heteroatom or where there is a second heteroatom selected from the group consisting of nitrogen, oxygen and sulfur, said 5- or 6- ring being unsubstituted or substituted by lower alkyl, amino or mono- or di- lower alkyl amino.

These novel compounds of the present invention are characterized by two novel aspects:

1. A ring formed between the nitrogen atom and the sulphur atom in the 2-mercaptoquinolone skeleton is thiazetidine; and
2. The quinoline skeleton is substituted with fluoro and cyclic amine as above defined at the 8- and 7-positions, respectively.

When $R^1$ and/or $R^2$ are alkyl moieties, they are preferably methyl, ethyl, n-propyl, isopropyl, n-butyl, isobutyl, secbutyl or tert-butyl.

When the phenyl moiety of $R^1$ is substituted by halogen, it may be substituted with one or more fluoro, chloro, bromo or iodo moieties. Fluoro substitution is particularly preferred.

According to one embodiment of the present invention, $R^1$ is hydrogen, straight or branch chain alkyl of 1 to 4 carbon atoms, phenyl or halophenyl.

According to another embodiment of the present invention, $R^2$ is hydrogen or straight or branch chain alkyl of 1 to 4 carbon atoms.

According to a further embodiment of the present invention,

is pyrrolidino, piperidino, piperazino, morpholino or thiomorpholino unsubstituted or substituted by straight or branch chain alkyl of 1 to 4 carbon atoms, amino or mono- or di- alkyl amino wherein each alkyl moiety is straight or branch chain of 1 to 4 carbon atoms.

According to a further embodiment of the present invention, $R^1$ is hydrogen, straight or branch chain alkyl of 1 to 4 carbon atoms, phenyl or halophenyl; $R^2$ is hydrogen or straight or branch chain alkyl of 1 to 4 carbon atoms; and

is pyrrolidino, piperidino, piperazino, morpholino or thiomorpholino unsubstituted or substituted by straight or branch chain alkyl of 1 to 4 carbon atoms, amino or mono- or di- alkyl amino wherein each alkyl moiety is straight or branch chain of 1 to 4 carbon atoms.

According to a further embodiment of the present invention, $R^1$ is hydrogen, straight or branch chain alkyl of 1 to 4 carbon atoms, phenyl or fluorophenyl; $R^2$ is hydrogen or straight or branch chain alkyl of 1 to 4 carbon atoms; and,

is pyrrolidino, piperidino, piperazino, morpholino or thiomorpholino unsubstituted or substituted by straight or branch chain alkyl of 1 to 4 carbon atoms, amino or mono- or di- alkyl amino wherein each alkyl moiety is straight or branch chain of 1 to 4 carbon atoms.

According to a further embodiment of the present invention, the compound of formula (I) is in the form of a pharmaceutically acceptable salt. Suitable salts according to the present invention are salts with mineral acids such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid, methanesulfonic acid, ethanesulfonic acid, benezenesulfonic acid, toluenesulfonic acid, naphthalenesulfonic acid, camphorsulfonic acid and the like; and salts with alkali metals or alkali earth metals such as sodium, potassium, calcium and the like.

Preferred compounds, according to the present invention are those set forth in the examples below.

Method A

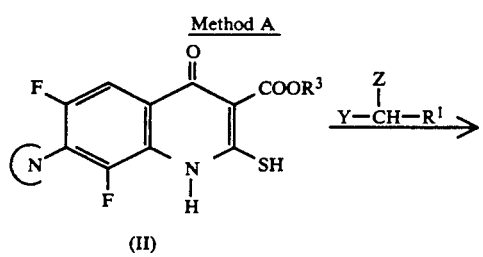

(II)

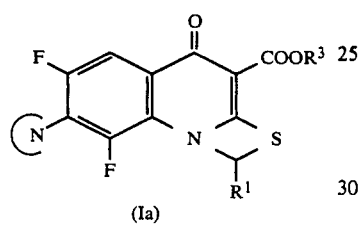

(Ia)

wherein R¹ and

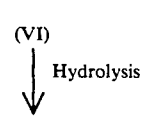

are as above defined; Y and Z are the same or different and each is halo; and R³ is alkyl, especially lower alkyl.

Method B (II)
↓ ZCH₂R¹

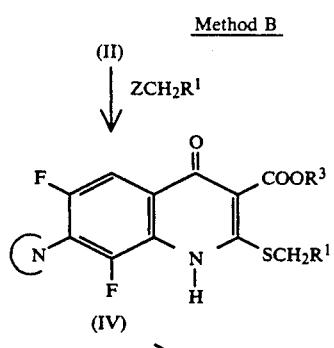

(IV)

Halogenating Agent →

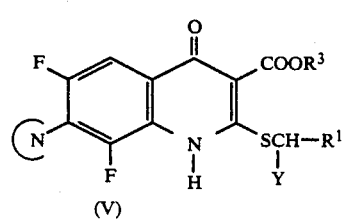

(V)

→ (Ia)

wherein R¹, R³ and

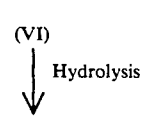

Y and Z are as above defined in Method A.

Method C

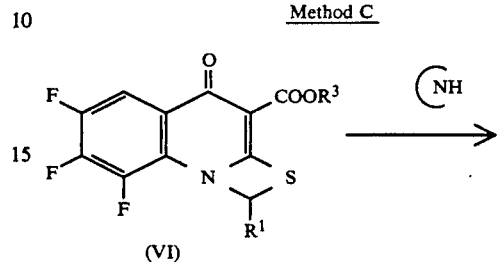

(VI)

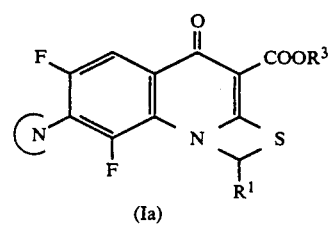

(Ia)

in which R¹, R³ and

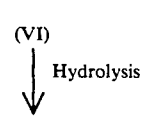

are as above defined in Method A.

Method D (VI)
↓ Hydrolysis

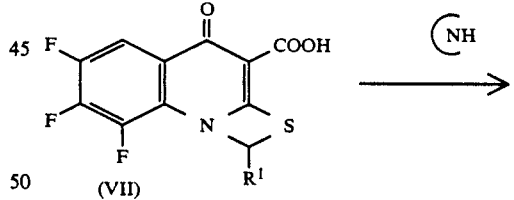

(VII)

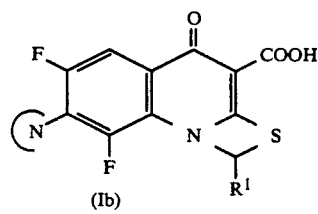

(Ib)

in which R¹ and

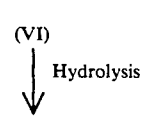

are as above defined.

As can be seen from the above procedures, the compounds of the present invention can be manufactured according to two techniques.

One is that the quinolinecarboxylic acid in which the 7-position is substituted with a cyclic amino group is used as a starting material and the thiazetidine ring is produced therefrom (Methods A and B). The second is that after formation of the thiazetidine ring, the cyclic amino group is introduced into the 7-position (Methods C and D). Each method is further illustrated below.

Method A: Compound (II) is reacted with a dihalide (e.g. methylene iodide, ethylidene bromide, benzylidene bromide, etc.) in an inert solvent in the presence of an acid removing agent (e.g. sodium carbonate, potassium carbonate, triethylamine, etc.) usually at 0° to 120° C. so that cyclization is carried out to give a compound (Ia).

For solvents, aprotic ones such as N,N-dimethylformamide, N,N-dimethylacetamide, dimethyl sulfoxide, sulforan, etc.) are suitable. The amount of the dihalide and acid-removing agent is not less than equimolar to one mole of (II) and is preferably 1.1 to 2.5 moles. In order to accelerate the reaction, 0.01 to 3.0 molar equivalents of sodium iodide or potassium iodide may be added to the reaction system.

Method B: Compound (II) is reacted with a halide ($ZCH_2R^1$ wherein Z and $R^1$ are as above defined) using the same solvent and acid-removing agent as in the method A usually at 0° to 80° C. to produce a compound (IV).

Then compound (IV) is halogenated in an inert solvent (e.g. halogenated hydrocarbon type solvent such as chloroform, dichloromethane, carbon tetrachloride, etc.) using a halogenating agent (e.g. N-bromosuccinimide, N-chlorosuccinimide, etc.) to produce a compound (V). Compound (V) is then cyclized using the same solvent and acid removing agent as in method A usually at 0° to 80° C. to give (Ia).

Method C: Condensation of compound (VI) with a cyclic amine gives a compound (Ia). This reaction is conducted in an inert solvent (e.g. aprotic solvent such as N,N-dimethylformamide, N,N-dimethylacetamide, dimethyl sulfoxide, sulforan, acetonitrile, etc.) preferably in the presence of an acid removing agent (e.g. sodium carbonate, potassium carbonate, sodium bicarbonate, potassium bicarbonate, triethylamine, etc.) usually at 0° to 80° C., for example at 40° to 60° C., using a cyclic amine as a reactant. The amount of the cyclic amine used is 1.5 to 2.5 moles to one mole of compound (VI).

Method D: Compound (VI) is hydrolyzed with an acid (e.g. concentrated sulfuric acid, fuming sulfuric acid, polyphosphoric acid or a mixture thereof) to give a compound (VII). This reaction is conducted using an excess of acid as a solvent (one to 30 times as much by weight or, preferably, 5 to 10 times as much) usually at 0° to 60° C. This hydrolyzing reaction may also be conducted in 20 to 30 times as much (preferably 5 to 10 times as much) 1% to 5% solution of potassium hydroxide or sodium hydroxide in aqueous alcohol (e.g. methanol, ethanol, propanol, butanol, etc.) usually at the temperature range of from room temperature to 60° C.

Then compound (VII) is reacted with a cyclic amine in the same solvent as in method C to give a compound (Ib). The reaction is usually conducted at 0° to 60° C. though 0° C. to room temperature is preferred.

Other methods described below can be used. For example, a compound of the formula (VIII) can be used as a starting material:

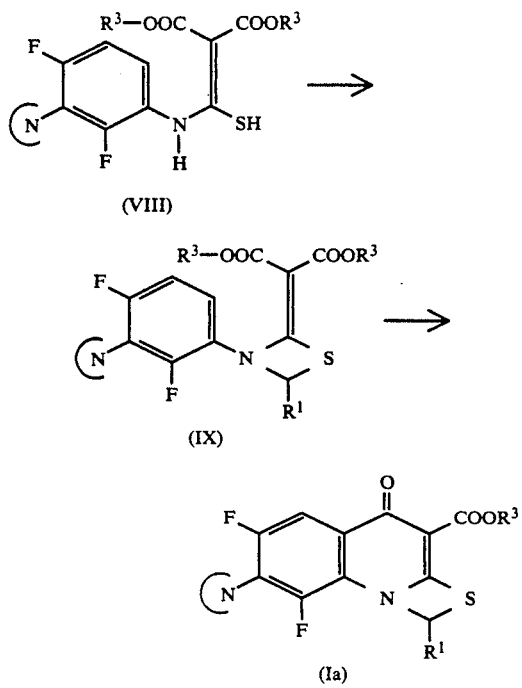

wherein $R^1$, $R^3$ and

are as above defined in the Method A.

Thus compound (VIII) is reacted with a dihalide in the presence of an acid removing agent (e.g. potassium carbonate) in an inert solvent (e.g. N,N-dimethylformamide, etc.). Then compound (IX) is subjected to a ring closure to give a compound (Ia). This ring closure reaction may be carried out by a method known per se such as, for example, by a method with heating or by a method using acidic substance such as phosphorus oxychloride, phosphorus pentachloride, phosphorus trichloride, thionyl chloride, fuming sulfuric acid, concentrated sulfuric acid, polyphosphoric acid, polyphosphate, etc. When an acid substance is used for example, one mole to great excess (preferably 20 to 30 moles) of acidic substance per mole of compound (IX) is used and the reaction temperature is usually 0° to 100° C. or, preferably, from 0° to 60° C.

Another method is that the thiazetidine ring is produced using 6,7,8-trifluoro compounds as a starting material, subjecting them to ring closure and condensation with an amine in the same manner as in method C to give a compound (Ia).

When a diamine such as piperazine is reacted in the above method, one nitrogen atom thereof may, if necessary, be protected by a method known per se and made to react with compound (VI) followed by removal of the protective group to give a desired compound having no substituent at the nitrogen.

Moreover, a substituent may be introduced onto a nitrogen atom to the N-unsubstituted one by a known method per se to afford an N-substituted diamino compound.

When the compounds prepared in accordance with the above method is an ester ($R^2$ is alkyl), it may, if and when desired, be hydrolyzed to give the corresponding carboxylic acid ($R^2$ is hydrogen). The hydrolysis can be conducted by the use of a great excess of acid (e.g. sulfuric acid, fuming sulfuric acid, hydrochloric acid, hydrobromic acid, hydrobromic acid/acetic acid, chlorosulfonic acid, polyphosphoric acid, etc.), preferably 10 to 20 times as much acid, as a solvent at the temperature of from room temperature to 110° C. Alternatively, the hydrolysis may be conducted by stirring at the temperature of from room temperature to 60° C. in 2 to 30 times as much volume (preferably 5 to 10 times a much volume) of 1 to 5% solution of potassium hydroxide or sodium hydroxide in aqueous alcohol such as methanol, ethanol, propanol or butanol (preferably, tert-butanol).

Further, the ester may be heated at 60°-150° C., preferably at 100°-110° C., with stirring in 10 to 100 times as much amount of alcohol corresponding to the desired ester in the presence of a catalytic amount of concentrated sulfuric acid so that the ester can be converted to desired another ester.

In the case of a carboxylic acid (i.e. $R^2$ is hydrogen), it can, if and when desired, be esterified to give desired ester (i.e. $R^2$ is alkyl). This esterification reaction can be conducted by a method known per se such as, for example, by the use of thionyl chloride with alcohol, condensing agent (e.g. dicyclocarbodiimide) with alcohol, or alkyl halide with alcoholate. Furthermore, in the case of a carboxylic acid, it can be used in a form of pharmacologically-acceptable salt such as sodium or potassium salt.

Both starting materials (II) and (VIII) are novel and such novel compounds can be manufactured by a known method (e.g. by a method disclosed in Japanese Laid Open 57/136588).

Novel starting material (VI) will be described below in reference examples and may be manufactured in accordance with the above methods A and B. Cyclic amines are known substances and can be manufactured by a known method.

Compound (I) as such can be isolated and purified by a method known per se such as, for example, concentration, pH conversion, transfer to another solvent, extraction with a solvent, crystallization, recrystallization, fractional distillation, chromatography, etc.

When the compounds of the present invention are administered as pharmaceuticals, to humans and animals, they are given per se or as a pharmaceutical composition containing, for example, 0.1 to 99.5% (more preferably, 0.5 to 90%) of active ingredient in combination with a pharmaceutically acceptable carrier.

The quinolinecarboxylic acid derivatives of the present invention may be given orally, parenterally, topically, or rectally. They are, of course, given by forms suitable for each administration route. For example, they are administered in tablet or capsule form, by injection, infusion, inhalation, eye lotion, ointment, suppository, etc. Administration may also be topical by lotion or ointment; and rectal by suppositories. Oral administration is preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginate, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically accetable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the dosage for treating bacterial infections a number of factors such as the age of the patient, body weight, severity of condition, administration route, and the like must be considered. Generally, 50 to 1000 mg is administered per day for a human adult preferably 100 to 300 mg per day for a human adult orally. In some cases, a lower dose is sufficient and, in some other cases, a higher dose or more doses may be necessary. The administration may be once a day or divided among administration several times a day.

It is preferred that the administration be divided so that it takes place 2 or 3 times per day.

The present invention will be more fully appreciated by those skilled in that art by reference to the examples set forth below.

REFERENCE EXAMPLES

Reference Example 1 Thiophosgene (1.4 g) was dissolved in 25 ml of ether, 2.0 g of triethylamine was added thereto with ice cooling and stirring (at not higher than 20° C.), then a mixture of 1.4 g of 2,3,4-trifluoroaniline and 3 ml of ether was gradually dropped thereinto at the same temperature, and the mixture was stirred for one hour at the same temperature. Then it was filtered off, the filtrate was concentrated, the residue was extracted with n-hexane, insoluble matters were removed by filtration, the resulting hexane-soluble matters were subjected to a silica gel column chromatography (Wacogel C-200 in the amount of 15 g) and eluted with n-hexane to give 1.39 g of 2,3,4-trifluorophenyl isothiocyanate.

REFERENCE EXAMPLE 2

Into 90 ml of dry tetrahydrofuran was suspended 2.0 g of 60% sodium hydride, 8.0 of diethyl malonate was dropped thereinto with stirring at room temperature, the mixture was stirred for one hour at the same temperature, a solution of 9.0 g of the compound obtained in Example 1 in 5 ml of dry tetrahydrofuran was dropped thereinto with stirring at room temperature and, one hour thereafter, 1.0 g of triethylamine was added, then 4.2 g of chloromethyl methyl ether was dropped thereinto, and the mixture was stirred for one hour. The reaction solution was poured over into ice water, extracted with ethyl acetate, washed with 1% hydrochloric acid, aqueous solution of sodium bicarbonate and aqueous solution of sodium chloride successively, and dried over anhydrous magnesium sulfate. Ethyl acetate was evaporated therefrom to give 18.3 g of diethyl 2,3,4-trifluorophenylaminomethoxymethylthiomethylenemalonate.

REFERENCE EXAMPLE 3

The compound obtained in Example 2 (18 g) was added to 100 ml of diphenyl ether and the mixture was stirred for 15 minutes at 230° C. with removal of ethanol therefrom in vacuo. After cooling, it was subjected to a silica gel column chromatography (300 g of Wakogel C-300 being used), diphenyl ether was eluted out with n-hexane and then eluted with chloroform to give 10.62 g of ethyl 6,7,8-trifluoro-4-hydroxy-2-methoxymethylthioquinoline-3-carboxylate.

REFERENCE EXAMPLE 4

The compound obtained in Example 3 (10. 5 g) was suspended in 60 ml of ethanol, 60 ml of concentrated hydrochloric acid was dropped thereinto, and the mixture was stirred at 50° C. for 1.5 hours. The reaction solution was poured over ice water, the crystals separated out therefrom were collected by filtration, washed with water, air-dried, and washed with n-hexane to give 6.8 g of ethyl 6,7,8-trifluoro-4-hydroxy-2-mercaptoquinoline-3-carboxylate.

REFERENCE EXAMPLE 5

To 25 ml of N,N-dimethylformamide were added 12 g of diiodoethane and 8.3 g of potassium carbonate, a solution of 6.07 g of the compound obtained in Example 4 dissolved in 60 ml of N,N-dimethylformamide was gradually dropped thereinto, and the mixture was stirred for 30 minutes at the same temperature. N,N-Dimethylformamide was evaporated therefrom in vacuo, the residue was dissolved in a mixture of chloroform and methanol (2:1), washed with water, dried over magnesium sulfate, the solvent was evaporated therefrom, and the crystals separated out therefrom were washed with ether to give 3.35 g of ethyl 6,7,8-trifluoro-1-methyl-4-oxo-4H-[1,3]thiazeto[3,2-a]quinoline-3-carboxylate.

EXAMPLE 1

Ethyl 6,8-difluoro-1-methyl-4-oxo-7-(1-piperazinyl)-4H-[1,3]thiazeto[3,2-a]quinoline-3-carboxyate Ethyl 6,7,8-trifluoro-1-methyl-4-oxo-4H-[1,3]thiazeto[3,2-a]quinoline-3-carboxylate (0.33 g) and 0.14 g of potassium carbonate were suspended in 10 ml of N,N-dimethylformamide, 0.13 g of anhydrous piperazine was added and the mixture was stirred at 60° C. for 2 hours. N,N-Dimethylformamide was evaporated therefrom in vacuo, the residue was dissolved in chloroform, the solution was washed with water, dried over magnesium sulfate, the solvent was evaporated therefrom, the residue was subjected to a silica gel column chromatography (30 g of Wakogel C-300 being used) and eluted with chloroform-methanol (4:1) to give 0.29 g of the title product, m.p. 195°–198° C. (decompn).

Elem. Anal. for $C_{18}H_{19}F_2N_3O_3S \cdot \frac{1}{2}H_2O$,
Calcd (%) C 54.06, H 4.91, N 10.51,
Found (%): C 54.12, H 5.02, N 10.35.

EXAMPLE 2

6,8-Difluoro-1-methyl-4-oxo-7-(1-piperazinyl)-4H-[1,3]thiazeto[3,2-a]quinoline-3-carboxylic acid To 0.5 g of ethyl 6,8-difluoro-1-methyl-4-oxo-7-(1-piperazinyl)-4H-[1,3]thiazeto[3,2-a]quinoline-3-carboxylate was added 10 ml of 5% solution of potassium hydroxide in a 3:1 mixture of tert-butanol and water and the mixture was stirred at 60° C. for 30 minutes. tert-Butanol was evaporated therefrom in vacuo and the residue was neutralized with acetic acid. After cooling, the crystals separated out therefrom were collected by filtration, washed with water and then washed with acetone and ether to give 0.43 g of the title product, m.p. 260° C. (decompn.).

Elem. Anal. for $C_{16}H_{15}F_2N_3O_3S \cdot \frac{3}{4}H_2O$,
Calcd (%): C 50.46, H 4.37, N 11.03,
Found (%): C. 50.29, H 4.54, N 10.97.

EXAMPLE 3

Ethyl 3 6,8-difluoro-1-methyl-7-(4-methyl-1-piperazinyl)-4-oxo-4H-[1,3]thiazeto[3,2-a]quinoline-3-carboxylate Ethyl 6,7,8-trifluoro-1-methyl-4-oxo-4H-[1,3]thiazeto-[3,2-a]quinoline-3-carboxylate (1.05 g) and 0.44 g of potassium carbonate were suspended in 20 ml of N,N-dimethylformamide, 0.48 g of N-methylpiperazine was added and the mixture was stirred at 60° C. for 6 hours. N,N-Dimethylformamide was evaporated therefrom in vacuo, the residue was dissolved in chloroform, the solution was washed with water, dried over magnesium sulfate, the solvent was evaporated therefrom, the residue was subjected to a silica gel column chromatography (50 g of Wakogel C-300 being used) and eluted with a 50:1 mixture of chloroform and methanol to give 0.79 g of the title product, m.p. 183°–185° C.

Elem. Anal. for $C_{19}H_{21}F_2N_3O_3S \cdot \frac{1}{4}H_2O$,
Calcd (%): C. 55.13, H 5.23) N 10.15,
Found (%): C. 54.99, H 5.29, N 10.12.

EXAMPLE 4

6,8-Difluoro-1-methyl-7-(4-methyl-1-piperazinyl)-4-oxo- [1,3]thiazeto[3,2-a]quinoline-3-carboxylic acid.

To 0.5 g of ethyl 6,8-difluoro-1-methyl-7-(4-methyl-1-piperazinyl)-4-oxo-4H-[1,3]thiazeto[3,2-a]quinoline-3-carboxylate was added 10 ml of 5% solution of potassium hydroxide in 3:1 mixture of tert-butanol and water and stirred at 60° C. for 30 minutes. tert-Butanol was evaporated therefrom in vacuo, the residue was neutralized with acetic acid, extracted with a 3:1 mixture of chloroform and methanol, the extract was washed with saturated sodium chloride solution, dried over magnesium sulfate, the solvent was evaporated therefrom, and the residue was subjected to a silica gel column chromatography (30 g of Wakogel C-300 being used) and eluted with chloroform-methanol (10:1) to give 0.18 g of desired product, m.p. 238° C. (decompn.).

Elem. Anal. for $C_{17}H_{17}F_2N_3O_3S \cdot \frac{1}{4}H_2O$,
Calcd (%): C. 52.91, H 4.57, N 10.89,
Found (%): C. 52.93, H 4.64, N 10.95.

Similarly prepared were the following compounds.

EXAMPLE 5

6,8-Difluoro-4-oxo-7-(1-piperazinyl)-4-oxo-4H-[1,3]thiazeto[3,2-a]quinoline-3-carboxylic acid.

Mass analysis ($C_{15}H_{13}F_2N_3O_3S$) $M^{30}$: 353.

EXAMPLE 6

Ethyl 6,8-difluoro-4-oxo-7-(1-piperazinyl)-4H-[1,3]thiazeto[3,2-a]quinoline-3-carboxylate.

Mass analysis ($C_{17}H_{17}F_2N_3O_3S$) $M^+$: 381

EXAMPLE 7

6,8-Difluoro-7-(4-methyl-1-piperazinyl)-4-oxo-4H-[1,3]thiazeto[3,2-a]quinoline-3-carboxylic acid Mass analysis ($C_{16}H_{15}F_2N_3O_3S$) $M^+$: 367.

EXAMPLE 8

Ethyl 6,8-difluoro-7-(4-methyl-1-piperazinyl)-4-oxo-4H-[1,3]thiazeto[3,2-a]quinoline-3-carboxylate Mass analysis ($C_{18}H_{19}F_2N_3O_3S$) $M^+$: 395.

EXAMPLE 9

7-(3-Amino-1-pyrrolidinyl)-6,8-difluoro-4-oxo-4H-[1,3]thiazeto[3,2-a]quinoline-3-carboxylic acid.

Mass analysis ($C_{15}H_{13}F_2N_3O_3S$) $M^+$: 353.

EXAMPLE 10

Ethyl 7-(3-amino-1-pyrrolidinyl)-6,8-difluoro-4-oxo-4H-[1,3]thiazeto[3,2-a]quinoline-3-carboxylate Mass analysis ($C_{17}H_{17}F_2N_3O_3S$) $M^+$: 381.

EXAMPLE 11

6,8-Difluoro-7-(3-methylamino-1-pyrrolidinyl)-4-oxo-4H-[1,3]thiazeto[3,2-a]quinoline-3-carboxylic acid Mass analysis ($C_{16}H_{15}F_2N_3O_3S$) $M^+$: 367.

EXAMPLE 12

Ethyl 6,8-difluoro-7-(3-methylamino-1-pyrrolidinyl)-4-oxo-4H-[1,3]thiazeto[3,2-a]quinoline-3carboxylate Mass analysis ($C_{18}H_{19}F_2N_3O_3S$) $M^+$: 395.

EXAMPLE 13

6,8-Difluoro-7-(3-methyl-1-piperazinyl)--4-oxo-4H-[3,2-a]quinoline-3-carboxylic acid.

Mass analysis ($C_{18}H_{19}F_2N_3O_3S$) $M^+$: 367.

EXAMPLE 14

Ethyl 6,8-difluoro-7-(3-methyl-1-piperazinyl)-4-oxo-4H-[1,3]thiazeto[3,2-a]quinoline-3-carboxylate Mass analysis ($C_{18}H_{19}F_2N_3O_3S$) $M^+$: 395.

EXAMPLE 15

6,8-Difluoro-7-(3,4-dimethyl-1-piperazinyl)-4-oxo-4H-[1,3]thiazeto[3,2-a]quinoline-3-carboxylic acid Mass analysis ($C_{17}H_{17}F_2N_3O_3S$) $M^+$: 381.

EXAMPLE 16

Ethyl 6,8-difluoro-7-(3,4-dimethyl-1-piperazinyl)-4-oxo-4H-[1,3]thiazeto[3,2-a]quinoline-3carboxylate Mass analysis ($C_{19}H_{21}F_2N_3O_3S$) $M^+$: 409.

EXAMPLE 17

6,8-Difluoro-7-thiomorpholino-4-oxo-4-H-[1,3]thiazeto[3,2-a]quinoline-3-carboxylic acid Mass analysis ($C_{16}H_{14}F_2N_3O_3S_2$) $M^+$: 384.

EXAMPLE 18

Ethyl 6,8-difluoro-7-thiomorpholino-4-oxo-4H-[1,3]thiazeto[3,2-a]quinoline-3-carboxylate Mass analysis ($C_{18}H_{18}F_2N_2O_3S_2$) M+: 412.

EXAMPLE 19

6,8-Difluoro-7-morpholino-4-oxo-4-H-[1,3]thiazeto[3,2-a]quinoline-3-carboxylic acid Mass analysis ($C_{16}H_{14}F_2N_2O_4S$) M+: 395.

EXAMPLE 20

Ethyl 6,8-difluoro-7-morpholino-4-oxo-4H-[1,3]thiazeto[3,2-a]quinoline-3-carboxylate.

Mass analysis ($C_{18}H_{18}F_2N_2O_4S$) M+: 396.

EXAMPLE 21

6,8-Difluoro-4-oxo-1-phenyl-7-(1-piperazinyl)-4H-[1,3]thiazeto[3,2-a]quinoline-3-carboxylic acid Mass analysis ($C_{21}H_{17}F_2N_3O_3S$) M+: 429.

EXAMPLE 22

Ethyl 6,8-difluoro-4-oxo-1-phenyl-7-(1-piperazinyl)-4H-[1,3]thiazeto[3,2-a]quinoline-3-carboxylate Mass analysis ($C_{23}H_{21}F_2N_3O_3S$) M+: 457.

EXAMPLE 23

6,8-Difluoro-7-(4-methyl-1-piperazinyl)-oxo-1-phenyl-4H-[1,3]thiazeto[3,2-a]quinoline-3-carboxylic acid Mass analysis ($C_{22}H_{19}F_2N_3O_3S$) M+: 443—,

EXAMPLE 24

Ethyl 6,8-difluoro-7-(4-methyl-1-piperazinyl)-4-oxo-1-phenyl-4H-[1,3]thiazeto[3,2-a]quinoline-3-carboxylate

EXAMPLE 24a 6,8-Difluoro-1-(4-fluorophenyl)-4-oxo-7-(1-piperazinyl)-4H-[1,3]thiazeto[3,2-a]quinoline-3-carboxylic acid Mass analysis ($C_{21}H_{16}F_3N_3O_3S$) M+: 447.
Mass analysis ($C_{24}H_{23}F_2N_3O_3S$) M+: 477.

EXAMPLE 25

Ethyl 6,8-difluoro-1-(4-fluorophenyl)-4-oxo-7-(1-piperazinyl)-4H-[1,3]thiazeto[3,2-a]quinoline-3-carboxylate Mass analysis ($C_{23}H_{20}F_3N_3O_3S$) M+: 475.

EXAMPLE 26

6,8-Difluoro-1-(4-fluorophenyl)-7-(4-methyl-1-piperazinyl)-4-oxo-4H-[1,3]thiazeto[3,2-a]quinoline-3-carboxylic acid Mass analysis ($C_{22}H_{18}F_3N_3O_3S$) M+: 461.

EXAMPLE 27

6,8-difluoro-1-(4-fluorophenyl)-7-(4-methyl-1-piperazinyl)-4-oxo-4H-[1,3]thiazeto[3,2-a]quinoline-3-carboxylate Mass analysis ($C_{24}H_{22}F_3N_3O_3S$) M+: 489.

EXAMPLE 28

6,8-Difluoro-1-(2,4-difluorophenyl)-4-oxo-7-(1-piperazinyl)-4H-[1,3]thiazeto[3,2-a]quinoline-3-carboxylic acid Mass analysis ($C_{21}H_{15}F_4N_3O_3S$) M+: 465.

EXAMPLE 29

Ethyl 6,8-difluoro-1-(2,4-difluorophenyl)-4-oxo-7-(1-piperazinyl)-4H-[1,3thiazeto[3,2-a]quinoline-3-carboxylate

EXAMPLE 30

6,8-Difluoro1-(2,4-difluorophenyl)-7-(4-methyl-1-piperazinyl)-4-oxo-4H-[1,3]thiazeto[3,2-a]quinoline-3-carboxylic acid.

Mass analysis ($C_{22}H_{17}F_4N_3O_3S$) M+: 479.

EXAMPLE 31

Ethyl 6,8-difluoro-1-(2,4-difluorophenyl)-7-(4-methyl-1-piperazinyl)-4-oxo-4H-[1,3]thiazeto[3,2-a]-quinoline-3-carboxylate Mass analysis ($C_{24}H_{21}F_4N_3O_3S$) M+: 507.
Mass analysis ($C_{23}H_{19}F_4N_3O_3S$) M+: 493.

EXAMPLE 32

6,8-Difluoro-1-(3,4-difluorophenyl)-4-oxo-7-(1-piperazinyl)-4H-[1,3]thiazeto[3,2-a]quinoline-3-carboxylic acid Mass analysis ($C_{26}H_{15}F_4N_3O_3S$) M+: 465.

EXAMPLE 33

Ethyl 6,8-difluoro-1-(3,4-difluorophenyl)-4-oxo-7-(1-piperazinyl)-4H-[1,3]thiazeto[3,2-a]quinoline-3carboxylate Mass analysis ($C_{28}H_{19}F_4N_3O_3S$) M+: 493.

EXAMPLE 34

6,8-Difluoro-1-(3,4-difluorophenyl)-7-(4-methyl-1-piperazinyl)-4-oxo-4H-[1,3]thiazeto[3,2-a]quinoline-3-carboxylic acid Mass analysis ($C_{22}H_{17}F_4N_3O_3S$) M+: 479.

EXAMPLE 35

Ethyl 6,8-difluoro-1-(3,4-difluorophenyl)-7-(4-methyl-1-piperazinyl)-4-oxo-4H-[1,3]thiazeto[3,2-a]quinoline-3-carboxylate.

Mass analysis ($C_{24}H_{21}F_4N_3O_3S$) M+: 507.

EXAMPLE 36

6,8-Difluoro-1-methyl-7-morpholino-4-oxo-4H-[1,3]thiazeto[3;2-a]quinoline-3-carboxylic acid Mass analysis M+: 368.

EXAMPLE 37

Ethyl 6,8-difluoro-1-methyl-7-morpholino--4-oxo-4H-[1,3]thiazeto-[3,2-a]quinoline-3-carboxylate Mass analysis M+: 396.

EXAMPLE 38

6,8-Difluoro-1-methyl-7-thiomorpholino-4-oxo-4H-[1,3]-thiazeto[3,2-a]quinoline-3-carboxylic acid Mass analysis M+: 384.

EXAMPLE 39

Ethyl 6,8-difluoro-1-methyl-7-thiomorpholino-4-oxo-4H-[1,3]thiazeto[3,2-a]quinoline-3-carboxylate Mass analysis M+: 412.

Melting points and analytical data of several of the above-identified compounds are given in the following table.

| Example Number | Melting Point ("d" means decompn.) | Molecular Formula | Elementary Analysis C (upper: calcd %, lower: found %) | H | N** |
|---|---|---|---|---|---|
| 5 | >300° C. | $C_{15}H_{13}F_2N_3O_3S \cdot H_2O$ | 48.51 | 4.07 | 11.31 |
|   |   |   | 48.75 | 4.11 | 11.07 |
| 6 | 220-230° C.(d) | $C_{17}H_{17}F_2N_3O_3S \cdot \tfrac{1}{2}H_2O$ | 52.30 | 4.65 | 10.76 |
|   |   |   | 52.42 | 4.59 | 10.68 |
| 7 | 239-252° C.(d) | $C_{16}H_{15}F_2N_3O_3S \cdot \tfrac{1}{2}H_2O$ | 51.06 | 4.28 | 11.16 |
|   |   |   | 51.23 | 4.01 | 10.96 |
| 8 | 227-230° C.(d) | $C_{18}H_{19}F_2N_3O_3S$ | 54.67 | 4.84 | 10.63 |
|   |   |   | 54.54 | 4.97 | 10.59 |
| 9 | 250° C.(d) | $C_{15}H_{13}F_2N_3O_3S \cdot \tfrac{1}{2}H_2O$ | 49.72 | 3.89 | 11.60 |
|   |   |   | 49.57 | 3.72 | 11.24 |
| 10 | 300° C.(d) | $C_{17}H_{17}F_2N_3O_3S \cdot H_2O$ | 51.12 | 4.79 | 10.52 |
|   |   |   | 50.70 | 4.35 | 10.50 |
| 13 | 300° C.(d) | $C_{16}H_{15}F_2N_3O_3S \cdot 2H_2O$ | 47.64 | 4.75 | 10.42 |
|   |   |   | 47.78 | 4.37 | 10.22 |
| 14 | 162° C.(d) |   |   |   |   |
| 15 | 223-224° C.(d) | $C_{17}H_{17}F_2N_3O_3S \cdot \tfrac{1}{2}H_2O$ | 52.30 | 4.64 | 10.52 |
|   |   |   | 52.46 | 4.59 | 10.72 |
| 16 | 229-230° C.(d) | $C_{19}H_{21}F_2N_3O_3S$ | 55.74 | 5.17 | 10.26 |
|   |   |   | 55.70 | 4.87 | 10.23 |
| 21 | 260-264° C.(d) | $C_{21}H_{17}F_2N_3O_3S \cdot \tfrac{1}{2}H_2O$ | 58.13 | 4.06 | 9.68 |
|   |   |   | 58.00 | 4.03 | 9.95 |
| 22 | 236-239° C.(d) | $C_{23}H_{21}F_2N_3O_3S \cdot \tfrac{1}{2}H_2O$ | 59.80 | 4.69 | 9.10 |
|   |   |   | 59.79 | 4.75 | 9.05 |
| 23 | 188-190° C.(d) | $C_{22}H_{19}F_2N_3O_3S \cdot 1/5H_2O$ | 59.11 | 4.37 | 9.40 |
|   |   |   | 59.10 | 4.47 | 9.28 |
| 24 | 216-218° C.(d) | $C_{24}H_{23}F_2N_3O_3S \cdot \tfrac{1}{2}H_2O$ | 60.56 | 4.98 | 8.83 |
|   |   |   | 60.77 | 5.12 | 8.71 |
| 24a | >300° C. | $C_{21}H_{16}F_3N_3O_3S \cdot \tfrac{1}{2}H_2O$ | 55.26 | 3.75 | 9.21 |
|   |   |   | 55.19 | 3.56 | 9.38 |
| 25 | 159-163° C.(d) | $C_{23}H_{20}F_3N_3O_3S \cdot 1/10H_2O$ | 57.88 | 4.26 | 8.80 |
|   |   |   | 57.83 | 4.31 | 8.66 |
| 26 | 268-271° C.(d) | $C_{22}H_{18}F_3N_3O_3S \cdot 11/10H_2O$ | 54.90 | 4.23 | 8.73 |
|   |   |   | 54.98 | 4.03 | 8.85 |
| 27 | 165-167° C.(d) | $C_{24}H_{22}F_3N_3O_3S$ | 58.89 | 4.53 | 8.58 |
|   |   |   | 58.69 | 4.59 | 8.57 |
| 28 | >300° C. | $C_{21}H_{15}F_4N_3O_3S \cdot \tfrac{1}{2}H_2O$ | 53.17 | 3.40 | 8.86 |
|   |   |   | 53.19 | 3.32 | 8.76 |
| 29 | 285° C.(d) | $C_{23}H_{19}F_4N_3O_3S \cdot \tfrac{1}{2}H_2O$ | 54.98 | 4.01 | 8.36 |
|   |   |   | 54.94 | 3.87 | 8.39 |
| 30 | 204-206° C.(d) | $C_{22}H_{17}F_4N_3O_3S \cdot \tfrac{1}{2}H_2O$ | 54.60 | 3.64 | 8.68 |
|   |   |   | 54.64 | 3.58 | 8.65 |
| 31 | 185-187° C. | $C_{24}H_{21}F_4N_3O_3S$ | 56.80 | 4.17 | 8.28 |
|   |   |   | 56.83 | 4.25 | 8.38 |
| 32 | >300° C. | $C_{21}H_{15}F_4N_3O_3S \cdot \tfrac{1}{2}H_2O$ | 53.17 | 3.40 | 8.86 |
|   |   |   | 53.11 | 3.40 | 9.03 |
| 33 | 278° C.(d) | $C_{23}H_{19}F_4N_3O_3S \cdot 1/10H_2O$ | 55.78 | 3.91 | 8.48 |
|   |   |   | 55.69 | 3.84 | 8.51 |
| 34 | 230-233° C.(d) | $C_{22}H_{17}F_4N_3O_3S$ | 55.11 | 3.57 | 8.76 |
|   |   |   | 54.89 | 3.64 | 8.60 |
| 35 | 190-192° C. | $C_{24}H_{21}F_4N_3O_3S \cdot 1/10H_2O$ | 56.60 | 4.20 | 8.25 |
|   |   |   | 56.52 | 4.10 | 8.12 |
| 36 | 245-246° C.(d) | $C_{16}H_{14}F_2N_2O_4S$ | 52.17 | 3.83 | 7.61 |
|   |   |   | 52.22 | 3.72 | 7.59 |
| 37 | 185-189° C. | $C_{18}H_{18}F_2N_2O_4S$ | 54.54 | 4.58 | 7.07 |
|   |   |   | 54.38 | 4.53 | 7.07 |
| 38 | 257° C.(d) | $C_{16}H_{14}F_2N_3O_3S$ | 50.00 | 3.67 | 7.29 |
|   |   |   | 49.90 | 3.70 | 7.32 |
| 39 | 188-190° C. | $C_{18}H_{18}F_2N_2O_3S_2$ | 52.42 | 4.40 | 6.79 |
|   |   |   | 52.32 | 4.51 | 6.71 |

DATA

The result of pharmacological test showing the usefulness of the representative compounds of the present invention is given below.

1. Measurement of minimum growth-inhibition concentrations (MIC).

Test Method: In accordance with a standard method by Japan Chemotherapeutic Society [Chemotherapy, 29(1), pages 76–79, 1981], agar plate dilution method was used and the MIC was measured. Thus, bouillon for measuring sensitivity was used and the bacterial liquid cultured at 37° C. for 18 hours was diluted to an extent of $10^6$ CFU/ml using said medium. This was inoculated to an agar medium containing drug for measuring sensitivity using a microplanter, cultured at 37° C. for 18 hours, and MIC was measured. Ofloxacin was used for comparison/control. The result is given in Table 1. It is apparent that the present invention compounds exhibit strong antibacterial activity against Pseudomonas aeruginosa and both gram-positive and negative bacteria.

TABLE 1

|  | The Present Invention Compd. | MIC ($\mu$/ml) Comparison/Control |
|---|---|---|
| Staphylococcus aureus 209-P JC-1 | 0.1 | 0.39 |
| Streptococcus pyogenes S-23 | 0.39 | 1.56 |
| Streptococcus pneumoniae Type I | 0.39 | 1.56 |
| Bacillus subtilis ATCC 6633 | 0.05 | 0.1 |
| Escherichia coli N1HJ JC-2 | 0.0125 | 0.1 |
| Klebsiella pneumoniae NCTC 9632 | 0.0125 | 0.05 |
| Serratia marcescens IFO 3736 | 0.1 | 0.78 |
| Proteus mirabilis IFO 3849 | 0.025 | 0.39 |
| Shigella flexneri 2a EW-10 | ≦0.00625 | 0.025 |
| Pseudomonas aeruginosa IFO-3445 | 0.1 | 1.56 |

"The Present Invention Compd" and "Comparison/Control" mean the compound of Example 2 and ofloxacin, respectively.

The above described test was additionally conducted on the compounds of the examples described below using the same microorganisms.

TABLE 2

| (MIC in $\mu$g/ml) Tested Compounds: | | | | | |
|---|---|---|---|---|---|
| Ex. 4 | Ex. 5 | Ex. 7 | Ex. 9 | Ex. 21 | Ex. 25 |
| 0.2 | 0.1 | 0.2 | 0.025 | 0.2 | 0.2 |
| 0.39 | — | — | — | — | — |
| 0.39 | — | — | — | — | — |
| 0.05 | 0.1 | 0.05 | 0.1 | 0.1 | 0.1 |
| 0.05 | 0.025 | 0.05 | 0.0125 | 0.1 | 0.1 |
| 0.025 | 0.025 | 0.0125 | 0.0125 | ≦0.00625 | ≦0.0625 |
| 0.2 | 0.05 | 0.1 | 0.1 | 1.56 | 1.56 |
| — | — | — | — | — | — |
| 0.0125 | 0.0125 | 0.025 | ≦0.00625 | 0.05 | 0.05 |
| 0.2 | 0.2 | 0.39 | 0.0125 | 0.39 | 0.39 |

2. Therapeutic effect on infections in mice.

Test method: E. Coli KC-14 and P. aeruginosa E-2 were suspended in 5% mucin and 0.5 ml of the suspension was injected intraperitoneally to ddY strain male mice (body weight: ca. 20 g; four weeks age; 10 mice per group). The amount of the bacteria inoculated was $5.1 \times 10^4$ CFU/mouse for E. coli and $7.5 \times 10^4$ CFU/mouse for P. aeruginosa. Drug was given orally once after 2 hours of inoculation and, out of the survival rate after one week, $ED_{50}$ was calculated by a Probit method. As to a comparison/control, ofloxacin was used. The result is given in Table 3.

TABLE 3

| Compound (Example No.) | $ED_{50}$ (mg/mouse) E. Coli | P. aeruginosa |
|---|---|---|
| 1 | 0.0046 | 0.09 |
| 2 | 0.0078 | 0.154 |
| Ofloxacin | 0.011 | 0.692 |

A similar test was conducted by inoculating E. coli KC-14 ($2.5 \times 10^5$ cfu/mouse) and P. aeruginosa E-2 ($1.25 \times 10^5$ cfu/mouse) and the result is given in Table 4.

TABLE 4

| | $ED_{50}$ (mg/mouse) The Present Invention Compd. | | | |
|---|---|---|---|---|
| | Ex. 2 | Ex. 4 | Ex. 7 | Ofloxian |
| E. coli KC-14 | 0.013 | 0.011 | 0.014 | 0.052 |
| P. aeruginosa E-2 | 0.156 | 0.177 | 0.263 | 0.521 |

It is clear from the above data that the compounds of the present invention are highly effective as antibacterial agents at lower doses than conventional bacterial agents not only against P. aeruginosa, but also against a broad range of gram-positive and gram-negative bacteria. Thus, the compounds of the present invention are highly effective against a wide spectrum of bacteria and exhibit very low toxicity and thus can be administered with a high degree of safety to humans and animals for the treatment of systemic local infections such as infectious diseases in the urinary gall tracts of humans and animals.

What is claimed is:

1. A compound of the formula (I)

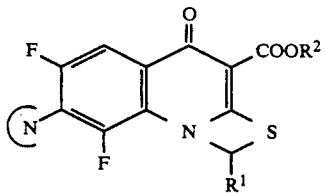

or a pharmaceutically acceptable salt thereof wherein $R^1$ is hydrogen, straight or branch chain lower alkyl of phenyl unsubstituted or substituted by one or more halo moieties; $R^2$ is hydrogen or straight or branch chain lower alkyl; and (N— is pyrrolidino, piperidino, piperazino, morpholino or thiomorpholino unsubstituted or substituted by straight or branch chain alkyl of 1 to 4 carbon atoms, amino or mono- or di- alkylamino wherein the alkyl moiety is straight or branch chain of 1 to 4 carbon atoms.

2. A compound according to claim 1 wherein $R^2$ is hydrogen, straight or branch chain alkyl of 1 to 5 carbon atoms, phenyl or halophenyl.

3. A compound according to claim 1 wherein R¹ is hydrogen or straight or branch chain alkyl of 1 to 4 carbon atoms.

4. A compound according to claim 1 wherein R¹ is hydrogen, straight or branch chain alkyl of 1 to 4 carbon atoms, phenyl or halophenyl; R² is hydrogen or straight or branch chain alkyl of 1 to 4 carbon atoms; and

is pyrrolidino, piperidino, piperazino, morpholino or thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

5. A compound according to claim 1 wherein R¹ is hydrogen, straight or branch chain alkyl of 1 to 4 carbon atoms, phenyl or fluorophenyl; R² is hydrogen or straight or branch chain alkyl of 1 to 4 atoms; and

is pyrrolidino, piperidino, piperazino, morpholino or thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

6. A compound according to claim 1 in the form of a pharmaceutically acceptable salt.

7. The compound according to claim 1 which is ethyl 6,8-difluoro-1-methyl-4-oxo-7-(1-piperazinyl)-4H-[1,3]-thiazeto[3,2-a]quinoline-3-carboxylate,6,8-difluoro-1-methyl-4-oxo-7-(1-piperazinyl)-4H-[1,3]thiazeto[3,2-a]quinoline-3-carboxylic acid, ethyl 6,8-difluoro-1-methyl-7-(4-methyl-1-piperazinyl)-4-oxo-4H-[1,3]thiazeto[3,2-a]quinoline-3-carboxylate, 6,8-difluoro-1-methyl-7-(4-methyl-1-piperazinyl)-4-oxo-4H-[1,3]thiazeto[3,2-a]quinoline-3-carboxylic acid, 6,8-difluoro-4-oxo-7-(1-piperazinyl)-4-oxo-4H-[1,3]thiazeto[3,2a-]quinoline-3-carboxylic acid, ethyl 6,8-difluoro-4-oxo-7-(-piperazinyl)-4H-[1,3]thiazeto[3,2-a]quinoline-3-carboxylate, 6,8-difluoro-7-(4-methyl-1-piperazinyl)-4-oxo-4H-[1,3]thiazeto[3,2-a]quinoline-3-carboxylic acid, ethyl 6,8-difluoro-7-(4-methyl-1-piperazinyl)-4-oxo-4H-[1,3]thiazeto-[3,2-a]quinoline-3-carboxylate, 7- (3-Amino-1-pyrrolidinyl)-6,8-difluoro-4-oxo-4H-[1,3]thiazeto[3,2-a]quinoline-3-carboxylic acid, ethyl 7-(3-amino-1-pyrrolidinyl)-6,8-difluoro-4-oxo-4H-[1,3]thiazeto[3,2-a]quinoline-3-carboxylate, 6,8-difluoro-7-(3-methylamino-1-pyrrolidinyl)-4-oxo-4H-[1,3]thiazeto[3,2-a]quinoline-3-carboxylic acid, ethyl 6,8-difluoro-7-(3-methylamino-1-pyrrolidinyl)-4-oxo-4H-[1,3]thiazeto[3,2-a]quinoline-3-carboxylate, 6,8-difluoro-7-(3-methyl-1-piperazinyl)-4-oxo-4H-[1,3]thiazeto[3,2-a]quinoline-3-carboxylic acid, ethyl6,8-difluoro-7-(3-methyl-1-piperazinyl)-4-oxo-4H-[1,3]thiazeto[3,2-a]quinoline-3-carboxylate, 6,8-difluoro-7-(3,4 -dimethyl-1-piperazinyl)-4-oxo-4H-[1,3]thiazeto[3,2-a]quinoline-3-carboxylic acid, ethyl 6,8-difluoro-7-(3,4-dimethyl-1-piperazinyl)-4-oxo-4H-[1,3]thiazeto[3,2- a]quinoline-3-carboxylate, 6,8-difluoro-7-thiomorpholino-4-oxo-4H-[1,3]thiazeto[3,2-a]quinoline-3-carboxylic acid, ethyl 6,8-difluoro-7-thiomorpholino-4-oxo-4H-[1,3]thiazeto[3,2-a]quinoline-3-carboxylate, 6,8-difluoro-7-morpholino-4-oxo-4H-[1,3]thiazeto[3,2-a]quinoline-3-carboxylic acid, ethyl 6,8-difluoro-7-morpholino-4-oxo-4H-[1,3]thiazeto[3,2-a]quinoline-3-carboxylate, 6,8-difluoro-4-oxo-1-phenyl-7-(1-piperazinyl)-4H-[1,3]thiazeto[3,2-a]quinoline-3-carboxylic acid, ethyl6,8-difluoro-4-oxo-1-phenyl-7-(1-piperazinyl) -4H-[1,3]thiazeto[3,2-a]quinoline-3-carboxylate, 6,8-difluoro-7-(4-methyl-1-piperazinyl)-4-oxo-1-phenyl-4H-[1,3]thiazeto[3,2-a]quinoline-3-carboxylic acid, ethyl 6,8-difluoro-7-(4-methyl-1-piperazinyl)-4-oxo-1-phenyl-4H-[1,3]thiazeto[3,2-a]quinoline-3-carboxylate, 6,8-difluoro-1-(4-fluorophenyl)-4-oxo-7-(1-piperazinyl)-4H-[1,3]thiazeto[3,2-a]quinoline-3-carboxylic acid, ethyl 6,8-difluoro-1-(4-fluorophenyl)-4-oxo-7-(1-piperazinyl)-4H-[1,3]thiazeto[3,2-a]quinoline-3-carboxylate, 6,8-difluoro-1-(4-fluorophenyl)-7-(4-methyl-1-piperazinyl)-4-oxo-4H-[1,3]thiazeto[3,2-a]quinoline-3-carboxylic acid, ethyl 6,8-difluoro-1-(4-fluorophenyl)-7-(4-methyl-1-piperazinyl)-4-oxo-4H-[1,3]thiazeto[3,2-a]quinoline-3-carboxylate, 6,8-difluoro-1-(2,4-difluorophenyl)-4-oxo-7-(1-piperazinyl)-4H-[1,3]thiazeto[3,2-a]quinoline-3-carboxylic acid, ethyl 6,8-difluoro-1-(2,4-difluorophenyl)-4-oxo-7-(1-piperazinyl)-4H-[1,3]thiazeto[3,2-a]quinoline-3-carboxylate, 6,8-difluoro-1-(2,4-difluorophenyl)-7-(4-methyl-1-piperazinyl)-4-oxo-4H-[1,3]thiazeto[3,2-a]quinoline-3-carboxylic acid, ethyl 6,8-difluoro-1-(2,4-difluorophenyl)-7-(4-methyl-1-piperazinyl)-4-oxo-4H-[1,3]thiazeto[3,2-a]quinoline-3-carboxylate, 6,8-difluoro-1-(3,4-difluorophenyl-4-oxo-7-(1-piperazinyl)-4H-[1,3]thiazeto[3,2-a]quinoline-3-carboxylic acid, ethyl 6,8-difluoro-1-(3,4-difluorophenyl)-4-oxo-7-(1-piperazinyl)-4H-[1,3]thiazeto[3,2-a]quinoline-3carboxylate6,8-difluoro-1-(3,4-difluorophenyl)-7-(4-methyl-1-piperazinyl)-4-oxo-4H-[1,3]thiazeto[3,2-a]quinoline-3-carboxylic acid, ethyl 6,8-difluoro-1-(3,4-difluorophenyl)-7-(4-methyl-1-piperazinyl)-4-oxo-4H-[1,3]thiazeto[3,2-a]quinoline-3-carboxylate or 6,8-difluoro-1-methyl-7-morpholino-4-oxo-4H-[1,3]thiazeto[3,2-a]quinoline-3-carboxylic acid.

8. A pharmaceutical composition useful for treating bacterial infections in humans and animals which comprises an anitbacterially effective amount of a compound of the formula (I)

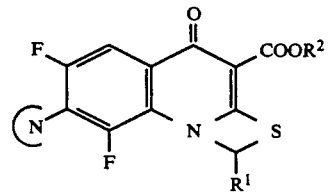

or a pharmaceutically acceptable salt thereof wherein R¹ is hydrogen, straight or branch chain lower alkyl or phenyl unsubstituted or substituted by one or more halo moieties; R² is hydrogen or straight or branch chain lower alkyl; and $\underset{\diagdown}{\diagup} N-$ is pyrrolidino, piperidino, piperazino, morpholino or thiomorpholino unsubstituted or substituted by straight or branch chain alkyl of 1 to 4 atoms, amino or mono- or di- alkylamino wherein the alkyl moiety is straight or branch chain of 1 to 4 carbon atoms, in combination with a pharmaceutically acceptable carrier.

9. A composition according to claim 8 wherein $R^1$ is hydrogen, straight or branch chain alkyl of 1 to 4 carbon atoms, phenyl or halophenyl.

10. A composition according to claim 8 wherein $R^2$ is hydrogen or straight or branch chain alkyl of 1 to 4 carbon atoms.

11. A composition according to claim 8 wherein $R^1$ is hydrogen, straight or branch chain alkyl of 1 to 4 carbon atoms, phenyl or halophenyl; $R^2$ is hydrogen or straight or branch chain alkyl of 1 to 4 carbon atoms; and $\underset{\diagdown}{\diagup} N-$ is pyrrolidino, piperidino, piperazino, morpholino or thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

12. A composition according to claim 8 wherein $R^1$ is hydrogen, straight or branch chain alkyl of 1 to 4 carbon atoms, phenyl or fluorophenyl; $R^2$ is hydrogen or straight or branch chain alkyl of 1 to 4 carbon atoms; and $\underset{\diagdown}{\diagup} N-$ is pyrrolidino, piperidino, piperazino, morpholino, thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

13. A composition according to claim 8 wherein the compound is in the form of a pharmaceutically acceptable salt.

14. A composition according to claim 8 wherein the compound is ethyl 6,8-difluoro-1-methyl-4-oxo-7-(1-piperazinyl)-4H-[1,3]thiazeto[3,2-a]quinoline-3-carboxylate, 6,8-difluoro-1-methyl-4-oxo-7-(1-piperazinyl)-4H-[1,3]thiazeto[3,2-a]quinoline-3-carboxylic acid, ethyl 6,8-difluoro-1-methyl-7-(4-methyl-1-piperazinyl)-4-oxo-4H-[1,3]thiazeto[3,2-a]quinoline-3-carboxylate, 6,8-difluoro-1-methyl-7-(4-methyl-1-piperazinyl)-4-oxo-4H-[1,3]thiazeto[3,2-a]quinoline-3-carboxylic acid, 6,8-difluoro-4-oxo-7-(1-piperazinyl)-4-oxo-4H-[1,3]thiazeto[3,2-a]quinoline-3-carboxylic acid, ethyl 6,8-difluoro-4-oxo-7-(1-piperazinyl)-4H-[1,3]thiazeto[3,2-a]quinoline-3-carboxylate, 6,8-difluoro-7-(4-methyl-1-piperazinyl)-4-oxo-4H-[1,3]thiazeto[3,2-a]quinoline-3-carboxylic acid, ethyl6,8-difluoro-7-(4-methyl-1-piperazinyl)-4-oxo-4H-[1,3]thiazeto[3,2-a]quinoline-3-carboxylate, 7-(3-Amino-1-pyrrolidinyl)-6,8-difluoro-4-oxo-4H-[1,3]thiazeto[3,2-a]quinoline-3-carboxylic acid, ethyl 7-(3-amino-1-pyrrolidinyl)-6,8-difluoro-4-oxo-4H-[1,3]thiazeto[3,2-a]quinoline-3-carboxylate, 6,8-difluoro-7-(3-methylamino-1-pyrrolidinyl)-4-oxo-4H-[1,3]thiazeto[3,2-a]quinoline-3-carboxylic acid, ethyl 6,8-difluoro-7-(3-methylamino-1-pyrrolidinyl)-4-oxo-4H-[1,3]thiazeto[3,2-a]quinoline-3-carboxylate, 6,8-difluoro-7-(3-methyl-1-piperazinyl)-4-oxo-4H-[1,3]thiazeto[3,2-a]quinoline-3-carboxylic acid, ethyl 6,8-difluoro-7-(3-methyl-1-piperazinyl)-4-oxo-4H-[1,3]thiazeto[3,2-a]quinoline-3-carboxylate, 6,8-difluoro-7-(3,4-dimethyl-1-piperazinyl)-4 -oxo-4H-[1,3]thiazeto[3,2-a]quinoline-3-carboxylic acid, ethyl 6,8-difluoro-7-(3,4-dimethyl-1-piperazinyl)-4-oxo-4H-[1,3]thiazeto[3,2-a]quinoline-3-carboxylate, 6,8-difluoro-7-thiomorpholino-4-oxo-4H-[1,3]thiazeto[3,2-a]quinoline-3-carboxylic acid, ethyl 6,8-difluoro-7-thiomorpholino-4-oxo-4H-[1,3]thiazeto[3,2-a]quinoline-3-carboxylate, 6,8-difluoro-7-morpholino-4-oxo-4H-[1,3]thiazeto[3,2-a]quinoline-3-carboxylic acid, ethyl 6,8-difluoro-7-morpholino-4-oxo-4H-[1,3]thiazeto[3,2-a]quinoline-3-carboxylate, 6,8-difluoro-4-oxo-1-phenyl-7-(1-piperazinyl)-4H-[1,3]thiazeto[3,2-a]quinoline-3-carboxylic acid, ethyl 6,8-difluoro-4-oxo-1-phenyl-7-(1-piperazinyl)-4H-[1,3]thiazeto[3,2-a]quinoline-3-carboxylate, 6,8-difluoro-7-(4-methyl-1-piperazinyl)-4-oxo-1-phenyl-4H-[1,3]thiazeto[3,2-a]quinoline-3-carboxylic acid, ethyl 6,8-difluoro-7-(4-methyl-1-piperazinyl)-4-oxo-1-phenyl-4H-[1,3]thiazeto[3,2-a]quinoline-3-carboxylate, 6,8-difluoro-1- (4-fluorophenyl)-4-oxo-7-(1-piperazinyl)-4H-[1,3]thiazeto[3,2-a]quinoline-3-carboxylic acid, ethyl 6,8-difluoro-1-(4-fluorophenyl)-4-oxo-7-(1-piperazinyl)-4H-[1,3]thiazeto[3,2-a]quinoline-3-carboxylate, 6,8-difluoro-1-(4-fluorophenyl)-7-(4-methyl-1-piperazinyl)-4-oxo-4H-[1,3]thiazeto[3,2-a]quinoline-3-carboxylic acid, ethyl 6,8-difluoro-1-(4-fluorophenyl)-7-(4-methyl-1-piperazinyl)-4-oxo-4H-[1,3]thiazeto[3,2-a]quinoline-3-carboxylate, 6,8-difluoro-1-(2,4-difluorophenyl)-4-oxo-7-(1-piperazinyl)-4H-[1,3]thiazeto[3,2-a]quinoline-3-carboxylic acid, ethyl 6,8-difluoro-1-(2,4-difluorophenyl)-4-oxo-7-(1-piperazinyl)-4H-[ 1,3]thiazeto[3,2-a]quinoline-3-carboxylate, 6,8-difluoro-1-(2,4-difluorophenyl)-7-(4-methyl-1-piperazinyl)-4-oxo-4H-[1,3]thiazeto[3,2-a]quinoline-3-carboxylic acid, ethyl 6,8-difluoro-1-(2,4-difluorophenyl)-7-(4-methyl-1-piperazinyl)-4-oxo-4H-[1,3]thiazeto[3,2-a]-quinoline-3-carboxylate, 6,8-difluoro-1-(3,4-difluorophenyl-4-oxo-7-(1-piperazinyl)-4H-[1,3]thiazeto[3,2-a]quinoline-3-carboxylic acid, ethyl 6,8-difluoro-1-(3,4-difluorophenyl)-4-oxo-7-(1-piperazinyl)-4H-[1,3]thiazeto[3,2-a]quinoline-3-carboxylate, 6,8-difluoro-1-(3,4-difluorophenyl)-7-(4-methyl-1-piperazinyl)-4-oxo-4H-[1,3]thiazeto[3,2-a]quinoline-3-carboxylic acid, ethyl 6,8difluoro-1-(3,4-difluorophenyl)-7-(4-methyl-1-piperazinyl)-4-oxo-4H-[13]thiazeto[32-a-]-quinoline-3-carboylate, 6,8-difluro-1-methyl-7-morpholino-4-oxo-4H-[1,3]thiazeto[3,2-a]quinoline-3-carboxylic acid, ethyl 6,8-difluoro-1-methyl-7-morpholino-4-oxo-4H-[1,3]thiazeto-[3,2-a]quinoline-3-carboxylate, 6,8-difluoro-1-methyl-7-thiomorpholino-4-oxo-4H-[1,3]-thiazeto[3,2-a]quinoline-3-carboxylic acid or ethyl 6,8-difluoro-1-methyl-7-thiomorpholino-4-oxo-4H-[1,3]thiazeto[3,2-a]quinoline-3-carboxylate.

15. A method of treating bacterial infections in humans and animals which comprises administering to a human or animal in need thereof an anitbacterially effective amount of a compound of the formula (I)

[Structure I: quinoline-thiazeto core with F, F substituents, N ring, COOR² group, and R¹ substituent]

or a pharmaceutically acceptable sale thereof wherein R¹ is hydrogen, straight or branch chain lower alkyl or phenyl unsubstituted or substituted by one or more halo moieties; R² is hydrogen or straight or branch chain lower alkyl; and

[Structure: N-ring]

is pyrrolidino, piperidino, piperazino, morpholino or thiomorpholino unsubstituted or substituted by straight or branch chain alkyl of 1 to 4 carbon atoms, amino or mono- or di- alkylamino wherein the alkyl moiety is straight or branch chain of 1 to 4 atoms in combination with a pharmaceutically acceptable carrier.

16. A method according to claim 15 wherein R¹ is hydrogen, straight or branch chain alkyl of 1 to 4 carbon atoms.

17. A method according to claim 15 wherein R² is hydrogen, straight or branch chain alkyl of 1 to 4 carbon atoms, phenyl or halophenyl.

18. A method according to claim 15 wherein R¹ is hydrogen, straight or branch chain of 1 to 4 carbon atoms, phenyl or halophenyl; R² is hydrogen or straight or branch chain alkyl of 1 to 4 carbon atoms; and

[Structure: N-ring]

is pyrrolidino, piperidino, piperazino, morpholino or thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

19. A method according to claim 15 wherein R¹ is hydrogen, straight or branch chain alkyl of 1 to 4 carbon atoms, phenyl or fluorophenyl; R² is hydrogen or straight or branch chain alkyl of 1 to 4 carbon atoms; and

[Structure: N-ring]

is pyrrolidino, piperidino, piperazino, morpholino or thiomorpholino unsubstituted or substituted by straight or branch chain alkyl of 1 to 4 carbon atoms, amino or mono- or di- alkyl amino wherein the alkyl moiety is straight or branch chain of 1 to 4 carbon atoms.

20. A method according to claim 15 wherein the compound is in the form of a pharmaceutically acceptable salt.

21. A method according to claim 15 wherein the compound is ethyl 6,8-difluoro-1-methyl-4-oxo-7-(1-piperazinyl)-4H-[1,3]thiazeto[3,2-a]quinoline-3-carboxylate, 6,8-difluoro-1-methyl-4-oxo-7-(1-piperazinyl)-4H-[1,3]thiazeto[3,2-a]quinoline-3-carboxylic acid, ethyl 6,8-difluoro-1-methyl-7-(4-methyl-1-piperazinyl)-4-oxo-4H-[1,3]thiazeto[3,2-a]quinoline-3-carboxylate, 6,8-difluoro-1-methyl-7-(4-methyl-1-piperazinyl)-4-oxo-4H-[1,3]thiazeto[3,2-a]quinoline-3-carboxylic acid, 6,8-difluoro-4-oxo-7-(1-piperazinyl)-4-oxo-4H-[1,3]thiazeto[3,2-a]quinoline-3-carboxylic acid, ethyl 6,8-difluoro-4-oxo-7-(1-piperazinyl)-4H-[1,3]thiazeto[3,2-a]quinoline-3-carboxylate, 6,8-difluoro-7-(4-methyl-1-piperazinyl)-4-oxo-4H-[1,3]thiazeto[3,2-a]quinoline-3-carboxylic acid, ethyl 6,8-difluoro-7-(4-methyl-1-piperazinyl)-4-oxo-4H-[1,3]thiazeto[3,2-a]quinoline-3-carboxylate, 7-(3-Amino-1-pyrrolidinyl)-6,8-difluoro-4-oxo-4H-[1,3]thiazeto[3,2-a]quinoline-3-carboxylic acid, ethyl 7-(3-amino-1-pyrrolidinyl)-6,8-difluoro-4-oxo-4H-[1,3]thiazeto[3,2-a]quinoline-3-carboxylate, 6,8-difluoro-7-(3-methylamino-1-pyrrolidinyl)-4-oxo-4H-[1,3]thiazeto[3,2-a]quinoline-3-carboxylic acid, ethyl 6,8-difluoro-7-(3-methylamino-1-pyrrolidinyl)-4-oxo-4H-[1,3]thiazeto[3,2-a]quinoline-3-carboxylate, 6,8-difluoro-7-(3-methyl-1-piperazinyl)-4-oxo-4H-[1,3]thiazeto[3,2-a]quinoline-3-carboxylic acid, ethyl6,8-difluoro-7-(3-methyl-1-piperazinyl)-4-oxo-4H-[1,3]thiazeto[3,2-a]quinoline-3-carboxylate, 6,8-difluoro-7-(3,4-dimethyl-1-piperazinyl)-4-oxo-4H-[1,3]thiazeto[3,2 -a]quinoline-3-carboxylic acid, ethyl 6,8-difluoro-7-(3,4-dimethyl-1-piperazinyl)-4-oxo-4H-[1,3]thiazeto[3,2-a]quinoline-3-carboxylate, 6,8-difluoro-7-thiomorpholino-4-oxo-4H-[1,3]thiazeto[3,2-a]quinoline-3-carboxylic acid, ethyl 6,8-difluoro-7-thiomorpholino-4-oxo-4H-[1,3]thiazeto[3,2-a]quinoline-3-carboxylate, 6,8-difluoro-7-morpholino-4-oxo-4H-[1,3]thiazeto[3,2-a]quinoline-3-carboxylic acid, ethyl6,8-difluoro-7-morpholino-4-oxo-4H-[1,3]thiazeto[3,2-a]quinoline-3-carboxylate, 6,8-difluoro-4-oxo-1-phenyl-7-(1-piperazinyl)-4H-[1,3]thiazeto[3,2-a]quinoline-3-carboxylic acid, ethyl6,8-difluoro-4 -oxo-1 -phenyl-7- (1-pipe razinyl)-4H-[1,3]thiazeto[3,2-a]quinoline-3-carboxylate, 6,8-difluoro-7-(4-methyl-1-piperaziny)-4-oxo-1-phenyl-4H-[1,3]thiazeto[3,2-a]quinoline-3-carboxylic acid, 1-piperazinyl)-4-oxo-1-phenyl-4H-[1,3]thiazeto[3,2]ethyl 6,8-difluoro-7-(4-methyl-quinoline-3-carboxylate, 6,8-difluoro-1-(4-fluorophenyl)-4-oxo-7-(1-piperazinyl)-4H-[1,3]thiazeto[3,2-a]quinoline-3-carboxylic acid, ethyl 6,8-difluoro-1-(4-fluorophenyl)-4-oxo-7-(1-piperazinyl)-4H-[1,3]thiazeto[3,2-a]quinoline-3-carboxylate, 6,8-difluoro-1-(4-fluorophenyl)-7-(4-methyl-1-piperazinyl)-4-oxo-4H-[1,3]thiazeto[3,2-a]quinoline-3-carboxylic acid, ethyl 6,8-difluoro-1-(4-fluorophenyl)-7-(4-methyl-1-piperazinyl)-4-oxo-4H-[1,3]thiazeto[3,2-a]quinoline-3-carboxylate, 6,8-difluoro-1-(2,4-difluorophenyl)-4-oxo-7-(1-piperazinyl)-4H-[1,3]thiazeto[3,2-a]quinoline-3-carboxylic acid, ethyl 6,8-difluoro-1-(2,4-difluorophenyl)-4-oxo-7-(1-piperazinyl)-4H-[1,3]thiazeto[3,2-a]quinoline-3-carboxylate, 6,8-difluoro-1-(2,4-difluorophenyl)-7-(4-methyl-1-piperazinyl)-4-oxo-4H-[1,3]thiazeto[3,2-a]quinoline-3-carboxylic acid, ethyl 6,8-difluoro-1-(2,4- difluorophenyl)-7-(4-methyl-1-piperazinyl)-4-oxo-4H-[1,3]thiazeto[3,2-a]quinoline-3-carboxylate, 6,8-difluoro-1-(3,4-difluorophenyl-4-oxo-7-(1-piperazinyl)-4H-[1,3]thiazeto[3,2-a]quinoline-3-carboxylic acid, ethyl 6,8-difluoro-1-(3,4-difluorophenyl)-4-oxo-7-(1-piperazinyl)-4H-[1,3]thiazeto[3,2-a]quinoline-3-carboxylate, 6,8-difluoro-1-(3,4-difluorophenyl)-7-(4-methyl-1-piperazinyl)-4-oxo-4H-[1,3]thiazeto[3,2-a]quinoline-3-carboxylic acid, ethyl 6,8-difluoro-1-(3,4-difluorophenyl)-7-(4-methyl-1-piperazinyl)-4-oxo-4H-[1,3]thiazeto[3,2-a]quinoline-3-carboxylate or 6,8-difluoro-1-methyl-7-morpholino-4-oxo-4H-[1,3]thiazeto[3,2-a]quinoline-3-carboxylic acid.

* * * * *